United States Patent [19]

Van Zile

[11] Patent Number: 4,834,081
[45] Date of Patent: May 30, 1989

[54] TOOL FOR REMOVING MODULAR JOINT PROSTHESIS

[75] Inventor: Richard R. Van Zile, Warsaw, Ind.

[73] Assignee: Boehringer Mannheim Corporation, Indianapolis, Ind.

[21] Appl. No.: 142,146

[22] Filed: Jan. 11, 1988

[51] Int. Cl.$^4$ ............... A61B 17/00; A61B 17/18; A61F 5/04
[52] U.S. Cl. ............... 128/92 VT; 623/20
[58] Field of Search ............... 623/18, 20, 33, 19, 623/21–23; 29/264; 128/92 VT, 303 R; 433/161

[56] References Cited

U.S. PATENT DOCUMENTS

| | | | |
|---|---|---|---|
| 2,464,289 | 3/1949 | Border | 433/161 |
| 2,591,451 | 4/1952 | Lynch et al. | 29/264 X |
| 3,685,058 | 8/1972 | Tronzo | 128/92 VT X |
| 3,846,898 | 11/1974 | Kerr | 29/264 X |
| 3,934,272 | 1/1976 | Wearne et al. | 623/20 |
| 4,100,626 | 7/1978 | White | 623/21 |
| 4,167,047 | 9/1979 | Grundei et al. | 623/20 |
| 4,304,011 | 12/1981 | Whelan, III | 623/21 |
| 4,352,212 | 10/1982 | Green et al. | 623/18 X |
| 4,399,813 | 3/1983 | Barber | 128/92 VT |
| 4,423,721 | 1/1984 | Otte et al. | 128/92 VT X |
| 4,459,985 | 7/1984 | McKay et al. | 623/20 X |
| 4,549,319 | 10/1985 | Meyer | 128/92 VT X |
| 4,655,778 | 4/1987 | Koeneman | 623/18 X |
| 4,676,797 | 6/1987 | Anapliotis et al. | 623/18 |
| 4,714,471 | 12/1987 | Grundei | 623/20 |

FOREIGN PATENT DOCUMENTS

| | | | |
|---|---|---|---|
| 83/02555 | 8/1983 | PCT Int'l Appl. | 623/18 |
| 1022328 | 3/1966 | United Kingdom | 128/92 VT |
| 1371335 | 10/1974 | United Kingdom | 623/23 |

OTHER PUBLICATIONS

"Standard Tapers", from Machinery's Handbook, 20th edition, 1979, pp. 1722–1724.
The Medical Journal of Australia, 1-1934, p. 13.

Primary Examiner—Richard J. Apley
Assistant Examiner—David J. Bender
Attorney, Agent, or Firm—Perman & Green

[57] ABSTRACT

A tool for removal of a joint prosthesis intended for implantation in a body. The prosthesis includes a component adapted to be fixed to a long bone having an intramedullary canal and further includes an elongated male stem having a uniformly tapered outer surface. In order to accommodate the particular size of long bone to which the component is to be fixed, a properly sized female stem is attached to the male stem before the component is fixed to the long bone. The female stem is adapted to be received in the intramedullary canal for fixation thereto, and has a uniformly tapered inner surface, the angle of the taper being substantially similar to the angle of taper of the outer surface of the male stem. As a result, the male stem and female stem become locked together when the inner surface of the female stem engages the outer surface of the male stem. The tool serves to disengage is obtained the male stem from the female stem as well as to disengage the female stem from the bone.

1 Claim, 3 Drawing Sheets

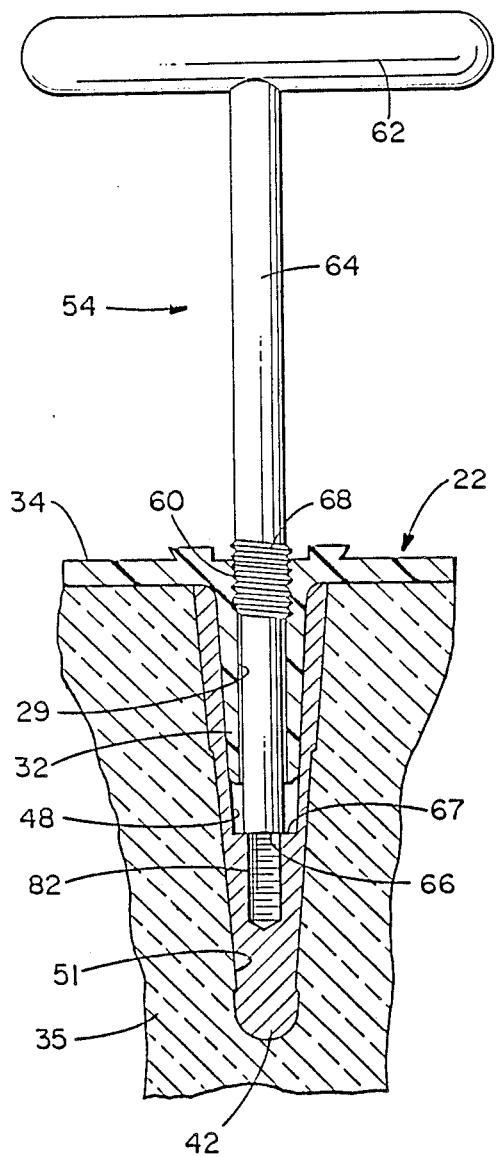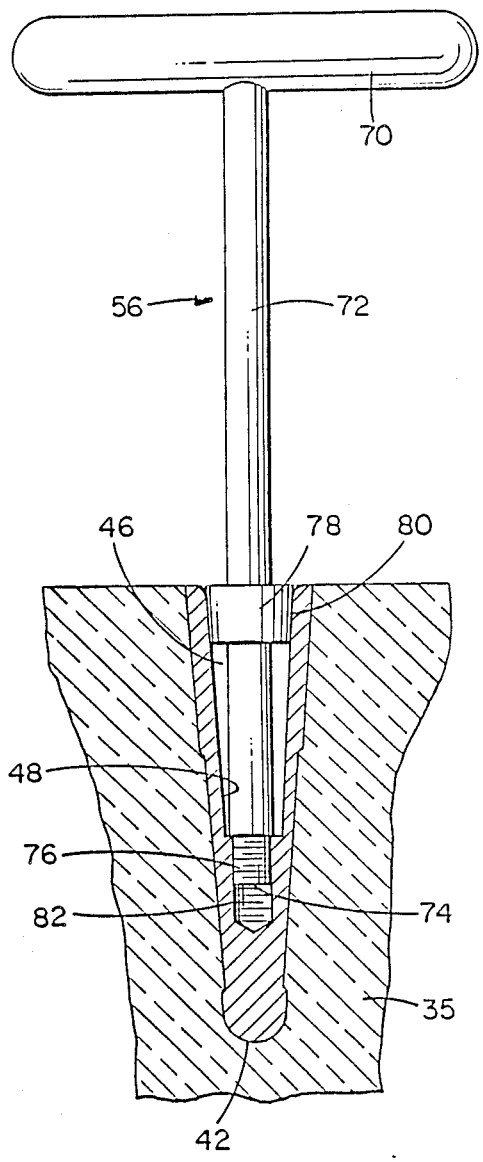

TOOL FOR REMOVING MODULAR JOINT PROSTHESIS

BACKGROUND OF THE INVENTION

1. Field of the Invention

The present invention relates generally to prosthetic joints and, more particularly, to a tool for removal from the bone of one component of a modular prosthetic joint construction which enables the revision of components having a broad range of sizes for long bones with a minimum inventory of prosthetic components.

2. Description of the Prior Art

While the present invention is applicable for use with implants of various types and in numerous applications in human and animal joints, it will be described herein, for purposes of example only, as being specifically adapted for use in regard to a knee joint prosthesis.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and articulate with the medial condyle and the lateral condyle of the tibia, respectively. The condyles of the tibia are substantially smooth and slightly cupped thereby providing a slight receptacle for receipt of the femoral condyles.

When the knee joint is injured whether as a result of an accident or illness, cartilage covering the natural bones may become damaged to the extent that they are unable to function (articulate) properly. If the bones are affected beyond the level or degree where natural healing and new growth will remedy the damage, then a prosthetic replacement of the damaged portion is called for in order to relieve pain and to restore normal use to the joint. Typically the entire joint is replaced by means of a surgical procedure which involves removal of the ends of the corresponding damaged bones and replacement of these ends with prosthetic implants. A typical such implant would be for the hip joint wherein a metal implant could be anchored in the intramedullary canal of the femur and would provide a generally spherical protuberance extending outwardly therefrom. The mating prosthetic portion would be a polyethylene socket member suitably anchored into the acetabulum. While prosthetic devices of this type, normally including a physiologically inert metal member and an engaging high density polyethylene member, are well known in the art, these types of devices are of a fixed and unchanging nature once they are inserted (implanted) into the patient and anchored there, whether by pinning or by acrylic bone cement or both.

Due in part to the fact that the size, shape and anatomy of virtually every patient is different, great care must be taken by the orthopedic surgeon in order to select properly sized and shaped prosthetic members for implanting. In order to achieve a suitable fit and size compatibility, an extensive number of a variety of each type of prosthetic implant must be available to the orthopedic surgeon from which he may choose. As a result, the cost of inventory as well as the logistics of ordering and storing a wide variety of prosthetic implants is cumbersome. Therefore, it would be an improvement to this present situation if prosthetic devices could be structured with removable portions such that there would be a reduction in inventory without a corresponding compromise as to the number and variety of different prosthetic combinations which can be created. In order to provide such an improvement, it is necessary that the prosthetic portions which are to be mixed and matched into a variety of combinations be suitably secured together so that the prosthetic member, which they in combination create, is not weaker nor more likely to fail than would be a similar prosthetic member constructed as a single integral piece.

A further concern involves the procedure when a prosthetic device becomes worn or damaged and a replacement must be made. While this is possible, it oftentimes involves elaborate surgery depending upon the particular portion of anatomy involved and the extent or nature of the damage to the prosthetic device. Furthermore, certain portions of the anatomy such as knee joints may be more susceptible to wear due to the surface area of articulation, the nature of the anatomy and the typical loads and forces which are encountered by this particular joint. Repair and/or replacement may also be desired when interfacing portions of the anatomy change and the contacting portion of the prosthesis needs to be revised as to its shape or size.

By structuring a prosthetic implant such that the portion most likely to wear or desired to be changed is quickly and easily replaceable from the remaining portion of the prosthetic implant, significant amounts of surgical time can be saved and the prosthesis can be more closely tailored to the patient's needs. Equally important is the fact that the portion of the prosthesis which is anchored into the patient, such as a tapered shaft inserted into the intramedullary canal of the tibia or of the femur, does not have to be surgically removed in order to make a replacement of a worn or damaged tibia articulation portion. Such a replaceable concept, in order to be effective, must securely hold the anchored portion and the replaceable portion together so as to act as an integral member regardless of the nature or complexity of the forces and loads acting thereon. With a design which achieves the requisite strength and durability, it is then possible to mix and match the replaceable portion with various anchored portions and vice versa such that, for example, an inventory of five relatively large and expensive replaceable portions and five relatively small and inexpensive anchoring portions for a tibial or femoral implant would be able to provide 25 different combinations of each to the orthopedic surgeon rather than having to inventory and stock 25 separate complete relatively large and expensive portions.

Tibial and femoral primary or revision prostheses that are presently being marketed have a fixed central stem, located on the distal plane of the tibial tray, or component, and on the proximal portion of the femoral component's anterior/posterior box. This stem is used primarily for purposes of stabilization and strength, both during installation and after the joint has been rebuilt. It is difficult to determine prior to surgery, even by x-raying, the size of the stem to be used. As a result, it is often necessary to wait until the bone structure is personally viewed by the surgeon during the implant operation before selecting the proper size of the implant and, particularly, the stem.

In the past, it has been necessary for hospitals to maintain a large inventory of sizes of prosthetic joint components in order to accommodate different sizes of patients. However, the cost of maintaining such a large inventory is substantial. This expense sometimes becomes so great that a hospital will maintain no inventory, but will order a particular prosthesis only when needed. As a result, if elective surgery is to be performed, oftentimes components are ordered specially for the surgery to be performed which includes one size larger and one size smaller than is expected to be used. Revision surgery in cases of traumatic injury could not be performed since there would be no inventory on hand to provide prompt availability for all possible patients.

Typical of the prior art known to the inventor which is broadly of interest when considering the invention are the U.S. Pat. Nos. 4,219,893 to Noiles and 4,257,129 to Volz. The Noiles patent discloses a prosthetic knee joint of the hinged type which permits rotation of the bones in two planes. In respect to the tibial component, a tibia stem whose upper part is rotatably engaged with the femoral component has a lower vertically depending rod which is rotatably received within a tibia sleeve which, in turn, is adapted to be implanted in the intramedullary canal of the tibia. The Volz patent is merely representative of a wide range of patents which disclose a tibial component having a downwardly extending stem for anchoring it to the tibia. A plastic bearing member is dove-tailed into receptive engagement on the upper surface of a support shelf and is held against further movement, once installed, by means of a vertical pin member which is received through the bearing and into a longitudinal bore formed in the stem and extending longitudinally in an axial direction. In neither patent is there a suggestion that the construction would enable the provision of various lengths and diameters of stems.

It is also known, in the instance of hip prostheses, for hospitals to inventory a number of femoral components for a hip prosthesis having a range of different sized heads for articulation in associated acetabular bearing components having a similar range of sizes. In some instances, stem extensions have been utilized in order to more readily accommodate a wide range of body sizes.

Although the foregoing devices have generally satisfied the goals for which they were intended, none offered the simplicity and economy which represent goals which have been achieved by the present invention.

SUMMARY OF THE INVENTION

To this end, the invention relates to a tool for removal of a modular joint prosthesis intended for implantation in a body. One component of the prosthesis is adapted to be fixed to a long bone having an intramedullary canal includes an elongated male stem having a uniformly tapered outer surface. In order to accommodate the particular size of long bone to which the component is to be fixed, another component, namely a properly sized female stem is attached to the male stem before the male stem is implanted into the long bone. The female stem is adapted to be received in the intramedullary canal for fixation thereto, and has a uniformly tapered inner surface, the angle of the taper being substantially similar to the angle of taper of the outer surface of the male stem. As a result, the male stem and female stem become locked together when the inner surface of the female stem engages the outer surface of the male stem. The proper size of female stem is obtained by selecting it from a family of female stems having a graduated sequence of different external dimensions.

A specialized tool is disclosed which can be used to remove the female stem of such a modular joint prosthesis whenever it should become necessary or desirable to do so. The novel tool is of simplified construction and can be readily attached to the female stem or disengaged from the female stem in the course of the surgical procedure.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 4 is a side elevation view, certain parts cut away and shown in section, to illustrate an extraction tool for disengaging a male stem from a female stem;

FIG. 5 is a side elevation view, certain parts cut away and shown in section, to illustrate a different extraction tool for removing a female stem from the bone.

DETAILED DESCRIPTION OF THE PREFERRED EMBODIMENT

Figure 1:
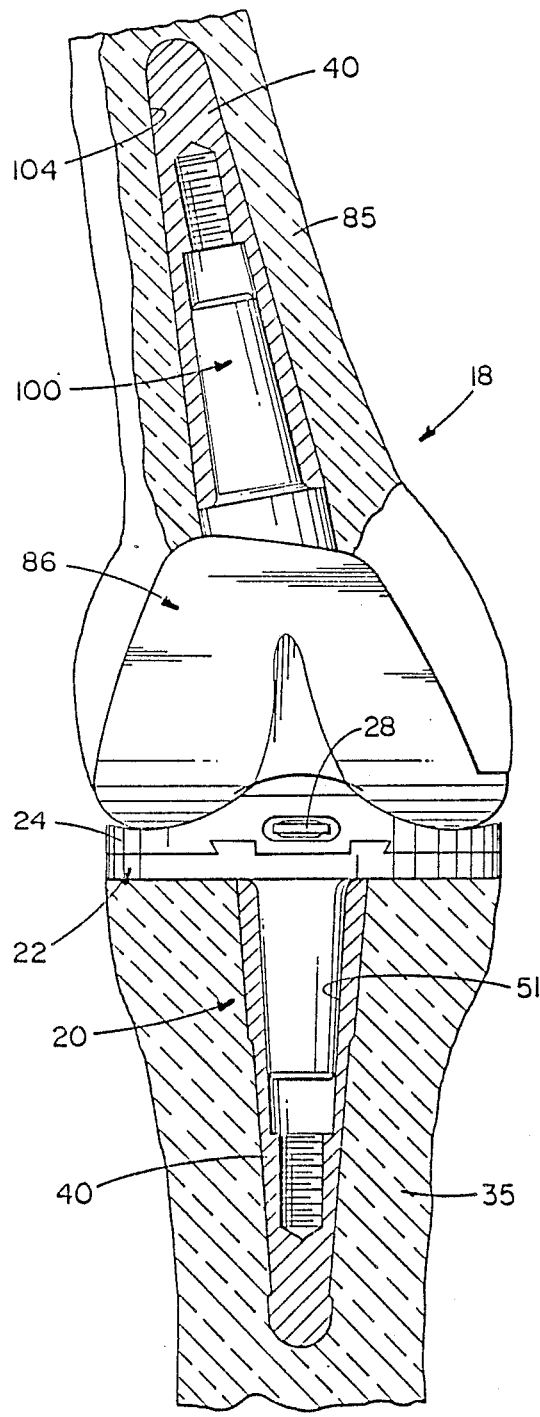
FIG. 1 is a front elevation view, partly in section, of a knee joint prosthesis which embodies the invention.

Turn now to the drawings and initially to FIG. 1 which illustrates a knee prosthesis 18 embodying the invention. One component of the knee prosthesis is a tibial implant 20 which, as more clearly seen in FIG. 2, includes a tibial tray 22, a replaceable bearing member 24, a vertical pin member 26, and a horizontal clip member 28. References to the terms "vertical" and "horizontal" are used in the normal context of such words wherein the tibia of an individual standing upright extends in a vertical direction.

Figure 2:
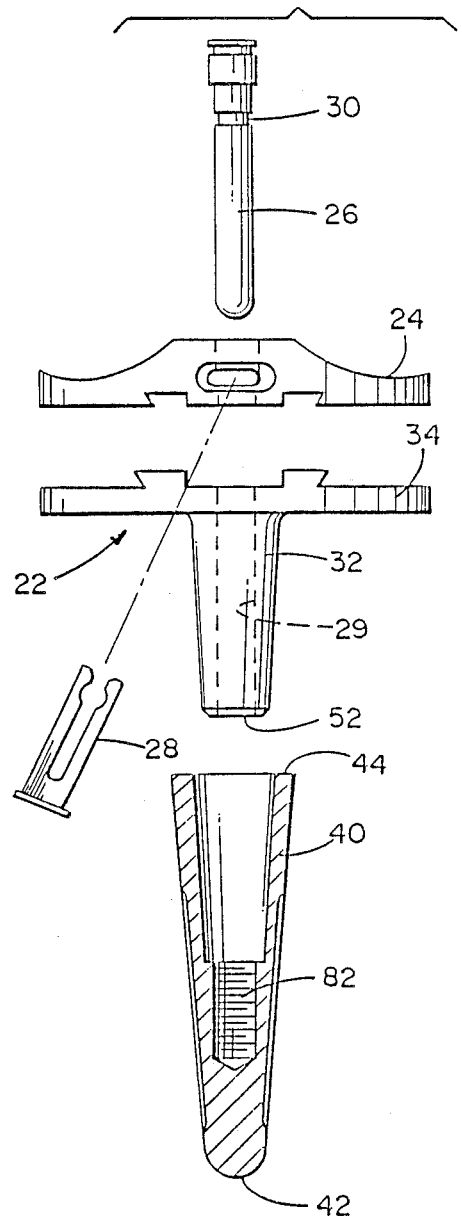
FIG. 2 is an exploded view, certain parts being cut away and in section illustrating tibial components embodying the invention.

It is noteworthy that FIG. 2 is an exploded view and that the assembly of these four component parts into a single prosthetic implant involves anteriorly/posteriorly sliding the bearing member 24 into supporting engagement on the tibial tray by reason of their corresponding dovetail surfaces. Once this engagement is achieved, the pin member 26 is inserted downwardly in a vertical direction through a suitable hole in the bearing member and into a longitudinal bore 29 in the tray 22. The final assembly step is to insert the clip member 28 into a suitable slot in the bearing member enabling the prongs of the clip member to engage a reduced diameter groove 30 of the pin member and thereby prevent its unintended removal.

Figure 3:
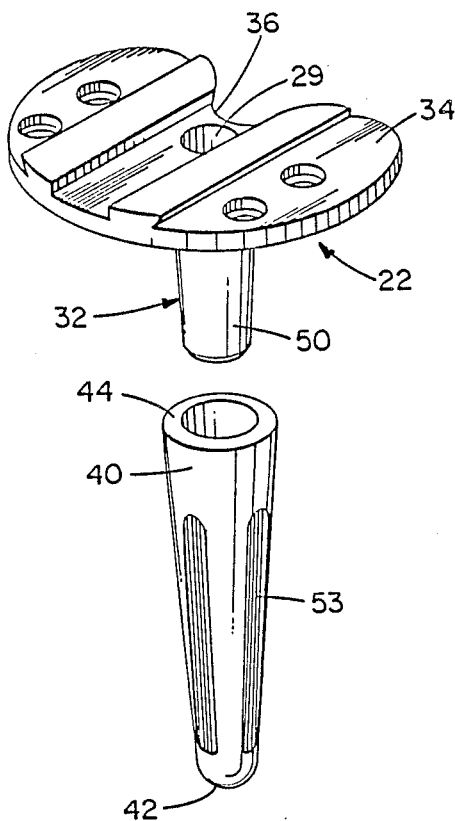
FIG. 3 is a perspective view of certain of the tibial components illustrated in FIGS. 1 and 2.

Referring to FIGS. 1-3, the tibial tray 22 is seen to include a tapered male stem 32 and a support shelf 34. The stem 32 is integrally joined to the support shelf and extends downwardly therefrom. The support shelf has a somewhat heart shaped configuration (see FIG. 3), generally conforming to the proximal end of the tibia 35 and defining a posterior depression 36 which provides a significant benefit to the implant in that this depression provides clearance for ligaments to pass therethrough without interference.

While the material choice for the tibial tray 22 and for the other prosthetic components discussed herein may vary, it is important that a relatively durable and strong material be used. Preferable materials are titanium, titanium alloy, or cobalt chrome although stainless steel, or even ceramics or composites could be employed. It is also important that the material selected be biologically and physiologically inert and that it be properly sterilized and prepared prior to implantation. Inasmuch as one aspect of the subject invention is the interchangeability of the prosthetic components, the shape and size characteristics of a female stem 40 may vary in a manner to be described. It is important, however, that the size and shape of the male stem 32 be standardized so that proper fit and engagement with any one of a family of female stems 40 can be achieved. The selection of a particular stem length and a articular tibial tray configuration is to be governed by the size, shape and anatomy of the particular patient as well as the nature and extent of the damaged bones.

As especially well seen in FIG. 1, the female stem 40 is, in effect, an extension member for the male stem 32. It may be fabricated from titanium bar stock or from cast cobalt chrome. Stainless steel, ceramics and composites are other suitable materials. Additionally, the male stem 32 and the female stem 40 can be of different materials so long as no galvanic reaction would occur as, for example, between stainless steel and cast cobalt chrome. In any event, the female stem 40 extends between a nose end 42 and an open tail end 44 to allow for insertion of the male stem 32 into a reception region 46 which is defined by an inner surface 48 uniformly tapered from the tail end 44 and extending a substantial distance in the direction of the nose end 42. The reception region 46 has a maximum inner diameter at the tail end 44 and a minimum inner diameter at the terminus of the inner surface 48 nearer to the nose end 42. The angle of taper of the inner surface 48 with respect to a longitudinal axis of the female stem 40 is substantially similar to the angle of taper of an outer surface 50 of the male stem 32. Similar to the inner surface 48, the outer surface 50 is uniformly tapered from a maximum outer diameter at a proximal end adjacent the support shelf 34 and a minimum outer diameter at a distal end 52 thereof.

The angular divergence between the inner surface 48 and the outer surface 50 lies generally within the range of ±3 minutes of arc. In this manner, when the female stem 40 is moved relative to the male stem 32 so that the surfaces 48 and 50 engage, the two components thereby achieve a locking engagement which cannot be broken except with the application of substantial force to again separate them. Indeed, substantially the entire surface 48 engages substantially the entire outer surface 50. This construction is referred to as a locking taper. Accordingly, once engaged, the male stem and the female stem operate as a single unit and have all of the attributes of a single stem of a similar size.

Although the outer shape of the female stem 40 is generally unimportant for purposes of the present invention, it may be desirable to interrupt its normally smooth surface with one or a plurality of flats 53. These serve to prevent rotation of the stem in the bone or in bone cement and, further, to reduce hoop stresses in the cement at the proximal tibia. The flats may be regularly or irregularly sized and spaced, as desired. While the outer shape may indeed be important for its reception and retraction within the intramedullary canal of the tibia, it otherwise has no effect on the ability of the female stem to matingly join with the male stem 32 and thereby achieve the benefits which have earlier been mentioned.

It was previously noted that a primary feature of the invention lay in its modularity. This feature arises by reason of the fact that a family or group of female stems 40 having a graduated sequence of different external dimensions are provided for locking engagement with the male stem 32 of a single prosthetic implant 20. It may be that the implant 20 is universally sized. However, even if two or more sizes of prosthetic implants 20 were to be used to accommodate different sizes of bodies, according to the invention, the male stem 32 would remain unchanged in size and shape as would the reception region 46 for a plurality of female stems 40. In this manner, a group of female stems 40 may be provided to accommodate the particular size of long bone to which the implant is to be fixed.

A typical family or group of female stems 40 of circular cross section might have the following relative dimensions:

| LENGTH (mm) | DIAMETER(S) (mm) |
| --- | --- |
| 50 | 10 |
| 70 | 10, 14 |
| 110 | 10, 14 |

In this typical family, the outer diameter of the female stem 40 at its tail end 44 remains constant for all the different sizes of stems. This dimension may typically be 20 mm. Those diameters noted above are the diameters at the rounded, or spherical, nose end 42. Although the foregoing dimensions are those for a stem 40 having a circular cross section, the particular cross sectional shape is arbitrary and need not be circular, just so long as the reception region 46 and, specifically, the inner surface 48, congruently matches that of the outer surface 50. Of course, a circular cross section would be desirable from the fabrication standpoint.

Another benefit which accrues from the construction just described arises when it is desired to remove the tibial implant 20 from the tibia for subsequent revision of the joint. In this instance, the tibial tray 34 and its associated male stem 32 can be removed from the female stem 40 without significant bone loss by use of a specialized extraction tool 54. Subsequently, if necessary, another specialized extraction tool 56 can be inserted into the reception region 46 of the stem 40 to remove the stem itself, if necessary. Of course, it might be desirable to allow the stem 40 to remain in place and reinsert the same tibial tray 34 or another one, as the case may be, again with minimum disruption of the surrounding bone.

The construction and operation of the extraction tool 54 for causing the male stem 32 to be disengaged from the female stem 40 will now be discussed with the aid of FIG. 4. As seen in FIG. 4, and as previously described, the tibial tray 22 is formed with a longitudinal bore 29 which extends through the support shelf 34 and through the male stem 32. The upper regions of the bore 29, those regions generally coextensive with the support shelf 34, are threaded as indicated at 60.

The extraction tool 54 has a handle 62 and a shank 64 fixed to the handle and extending to a tip end 66. The shank 64 is threaded, as at 68, intermediate the tip end 66 and the handle 62. In order to perform the extraction operation, as seen in FIG. 4, the shank 64 is inserted into the bore 29 until the threads 68 engage with the threads 60. The handle 62 is caused to rotate on the longitudinal axis of the shank 64 until the tip end 66 advances into engagement with the female stem 40 proximate to the nose end 42, specifically, a terminal surface 67. With continued rotation of the handle 62, the male stem is caused to be disengaged from the female stem whereupon the shank 64 can be unscrewed from the tibial tray 22 and the latter manually lifted away from the tibia.

Turn now to FIG. 5 for a description of the construction and operation of the extraction tool 56. Once the tibial tray 22 has been removed, the way is clear for the removal of the female stem 40 from the intramedullary canal 51 of the tibia. The extraction tool 56 includes a handle 70 and a shank 72 fixed to the handle and extending to a tip end 74. The shank 72 is threaded adjacent the tip end 74 as at 76. Also, an annular collar 78 is fixed to the shank 72 and lies in a plane transverse to the longitudinal axis of the shank at a location intermediate the handle 70 and the tip end 74. The collar 78 is formed with an outer peripheral surface 80 which is tapered to generally conform to the inner surface 48 of the female stem 40. For purposes of extraction, the female stem 40 is provided with a threaded bore 82 intermediate the inner surface 48 and the nose end 42. Thus, in order to extract the female stem 40 from the tibia, the shank 72 is inserted into the reception region 46 until the threads 76 at the tip end of the shank engage the threaded bore 82. The shank 72 is then rotated by means of a handle 70 so as to engage the threads 76 and 82. When this occurs, the outer peripheral surface 80 lightly engages the inner surface 48 to thereby stabilize the tool 56 relative to the stem 40. The handle 70 continues to be rotated until the threads 76 are firmly engaged with the threads 82. Thereupon, force is applied to the handle 70 generally along the longitudinal axis of the stem 40, that is, in a direction away from the bone, until extraction has been achieved. By pulling along the longitudinal axis of the stem 40 and by reason of the stability provided by the collar 78, the stem 40 is extracted with minimum disruption of the surrounding bone.

Figure 6:
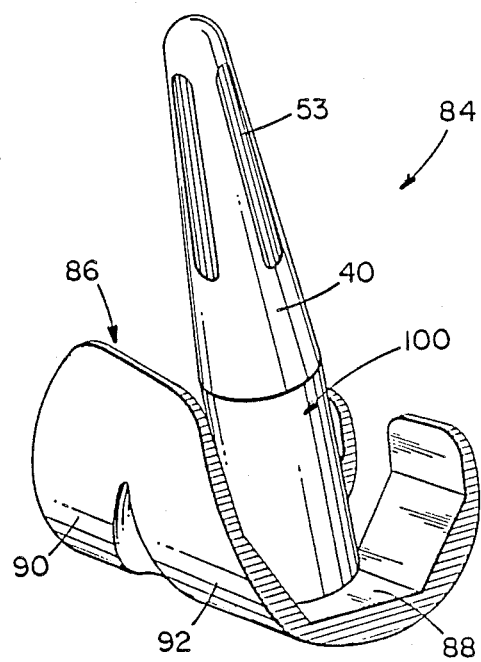
FIGS. 6, 7, and 8 are perspective, side elevation, and top plan views, respectively, of femoral components embodying the invention.
Figure 8:
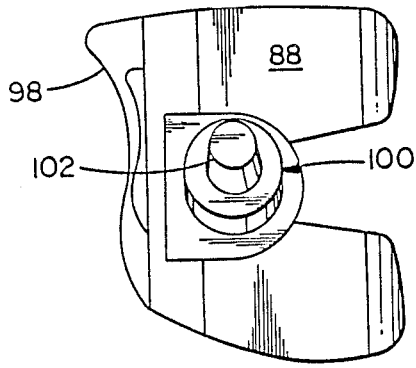
Figure 7:
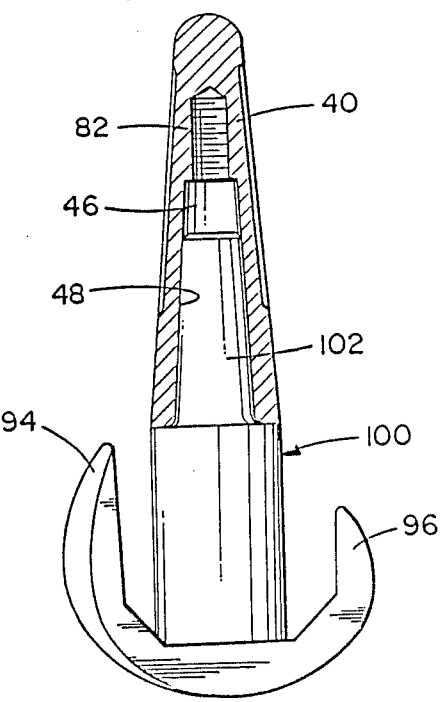

While the foregoing description has been directed toward the prosthetic implant 20 utilized in conjunction with the tibia 35, the concept of the invention is just as applicable to a prosthetic implant 84 for a knee applied to the femur 85 as also seen in FIG. 1. Thus, as more clearly seen with reference to FIGS. 4–6, the implant 84 comprises a U-shaped patella flange 86 which, in turn, includes a base 88 and a pair of condylar runners 90, 92 which extend between a higher anterior sidewall 94 and a lower posterior sidewall 96. A patella groove 98 between the condylar runners 90, 92 is provided for receiving and guiding the patella (not shown) in a known manner as the leg is caused to flex. A male stem 100 is integral with and upstanding from the base. At its lowermost regions, the stem 100 may be uniformly shaped and sized along its length, but at its uppermost regions is tapered in the manner of the stem 32. As with the stem 32, the cross sectional shape is arbitrary so long as it matches with that of the female stem 40 to be matingly engaged therewith. What is important is that an outer surface 102 is uniformly tapered in congruent fashion with the inner surface 48 of the female stem 40. As in the instance of the tibial implant 20, the female stem 40 is applied to the male stem 100 until their mutually facing surfaces engage and cause them to become locked together. Thereupon, the implant 84 is applied to the femur with the joined stems 40 and 100 received within the intramedullary canal 104 at the distal end of the femur.

Although the foregoing descriptions have concentrated on the application of the invention for purposes of knee prostheses, it need not be so limited, but has application in any instance involving joints between long bones and permits the accommodation of a wide range of sizes of long bones by providing a family of relatively inexpensive female stems which can be universally joined with a single size, or small number of sizes, of larger, more expensive, primary components.

While preferred embodiments of the invention have been disclosed in detail, it should be understood by those skilled in the art that various other modifications may be mad to the illustrated embodiments without departing from the scope of the invention as described in the specification and defined in the appended claims.

What is claimed is:

1. For operation with a prosthetic component adapted to be fixedly received in the intramedullary canal of a long bone, the prosthetic component being a female stem extending between a nose end and an open tail end and having a uniformly tapered inner surface defining a reception region and having a maximum inner diameter at the tail end and a minimum inner diameter distant therefrom and having a threaded bore intermediate the inner surface and the nose end, a tool for removal of the prosthetic component from the intramedullary canal of the long bone comprising:

a handle; and
   a shank fixed to said handle and extending between a proximal end adjacent said handle and a distal end, said shank being receivable in the reception region and having external threads formed therein adjacent said distal end which are threadedly engageable with the stem within its bore; and
   an annular collar fixed to said shank and lying in a plane transverse to the longitudinal axis thereof intermediate said proximal end and said distal end, said collar having an outer peripheral surface engageable with the inner surface when said shank is threadedly engaged with the stem to thereby stabilize the tool during the withdrawal operation;
   whereby, with the shank being threadedly engaged with the stem, and with force being applied to said handle in a direction away from the bone, the stem can be withdrawn from the intramedullary canal with minimum disruption of the bone.

* * * * *